(12) United States Patent
Herskovic

(10) Patent No.: US 11,964,029 B2
(45) Date of Patent: Apr. 23, 2024

(54) RADIOACTIVE CONDUIT AND METHOD FOR IN VIVO TREATMENT OF TUMORS

(71) Applicant: Arnold M. Herskovic, Chicago, IL (US)

(72) Inventor: Arnold M. Herskovic, Chicago, IL (US)

(*) Notice: Subject to any disclaimer, the term of this patent is extended or adjusted under 35 U.S.C. 154(b) by 0 days.

(21) Appl. No.: 17/707,863

(22) Filed: Mar. 29, 2022

(65) Prior Publication Data

US 2023/0310666 A1    Oct. 5, 2023

(51) Int. Cl.
*A61K 51/12* (2006.01)
*A61N 5/10* (2006.01)
*G21G 4/08* (2006.01)

(52) U.S. Cl.
CPC ........ *A61K 51/1282* (2013.01); *A61N 5/1027* (2013.01); *G21G 4/08* (2013.01); *A61L 2300/44* (2013.01); *A61N 2005/1024* (2013.01)

(58) Field of Classification Search
CPC ............ A61K 51/1282; A61K 51/1286; A61K 51/1289; A61N 5/1027; A61N 5/00; A61N 5/1001; A61N 2005/1024; G21G 2001/0084; G21G 4/08; A61L 2300/44
See application file for complete search history.

(56) References Cited

U.S. PATENT DOCUMENTS

| | | | | |
|---|---|---|---|---|
| 2002/0143228 A1* | 10/2002 | Chan | ............. | A61K 51/12 427/430.1 |
| 2004/0109823 A1* | 6/2004 | Kaplan | ............. | A61L 31/02 600/1 |
| 2015/0080847 A1* | 3/2015 | Cima | ............. | A61P 35/00 604/285 |
| 2015/0190654 A1* | 7/2015 | Herskovic | ............. | A61N 5/1007 600/7 |
| 2018/0028836 A1* | 2/2018 | Herskovic | ............. | A61K 51/0495 |

* cited by examiner

*Primary Examiner* — Nilay J Shah
(74) *Attorney, Agent, or Firm* — CHERSKOV FLAYNIK & GURDA, LLC

(57) ABSTRACT

The invention provides a system for the in vivo treatment of diseased tissue, the system comprising a first longitudinally extending surface and a second longitudinally extending surface coaxial to the first longitudinally extending surface to form a medicament carrying vehicle, wherein the vehicle defines a tunnel adapted to allow physiological fluid to pass through the vehicle. Also provided is method for treating, in vivo, diseased tissue, the method comprising inserting a housing into a tumor excision site and removably sliding a medicament vehicle within the vehicle so as to be encapsulated by the housing.

12 Claims, 5 Drawing Sheets

RADIOACTIVE CONDUIT AND METHOD FOR IN VIVO TREATMENT OF TUMORS

BACKGROUND OF THE INVENTION

1. Field of the Invention

This invention relates to a device and method for treating tumors and more specifically, this invention relates to a device and method for exposing in vivo cancerous tissue to radiation.

2. Background of the Invention

The radiation treatment of cancerous tissue is well known. However, standard treatments often result in exposure of healthy tissue to radiation. This collateral damage to healthy parenchyma leads to complications such as necrosis, discomfort, pain, and bleeding so as to ultimately confound treatment of the primary malady.

Collateral damage to healthy tissue due to radiation exposure can be particularly problematic during treatment, especially if that treatment is in the form of externally applied beam radiations. Treatments relying on radioactive stents or other sources inserted into the body helps ameliorate such collateral damage.

Cancers of, or within tubular physiologic structures present unique challenges. Persistence/recurrence of cancers after treatment (such as for esophageal cancers) are about 40 percent. Additionally, in palliative situations, most patients have obstruction issues which can be ameliorated by immediate obstruction relief via the stent and maintenance of that relief by brachytherapy radiations.

In most patients in the US and well developed countries, esophageal tumors tend to be adenocarcinomas and often extend to the gastric cardia. In addition, the occurrence of fistulas between the left main bronchus and the esophagus is a risk due to the proximity of the two structures. Brachytherapy stents have been used to treat such tissue venues but they nevertheless often increase the risk of fistulization, or slippage (undesirable dislocation or rotation). Such dislocation of stents occurs about 15 percent of the time in the esophagus and more frequently in other sites.

A need exists in the art for a system and method for treating cancerous tissue in vivo while eliminating or drastically minimizing (to less than 5 percent of the total amount of radiation dose present) non-therapeutic exposure of healthy tissue to the treatment radiation. The radiation media employed by the system and method can be remotely positioned (both physically and chemically). Furthermore, the radiation media should be individually encapsulated either in a separate vehicle within the system or integrally molded with other materials comprising the system.

SUMMARY OF INVENTION

An object of the invention is to provide a system and method for treating diseased tissue in vivo that overcomes many of the drawbacks of the prior art.

Another object of the invention is to provide a system and method for physically and chemically minimizing exposure of therapeutic radiation to healthy tissue during brachytherapy. A feature of the invention is a medicament vehicle removably received by a positioning housing. An advantage of the invention is that reshaping of the treated lumen is not required. Another advantage is that the system may be repositioned within a treatment venue (such as a tumor excise site) without first removing it from the patient.

Still another object of the invention is to provide an implantable device for exposing diseased tissue to radiation. A feature of the invention is that the surface of the device can be adapted to impart heat to the tissue simultaneous with the housing attenuating radiation emanating from inside the device. The scaffolding of the device may be a stent most often made from nitinol or other shaped memory material which exerts a radial pressure. An advantage of the device is that hot spots generated by over exposure to radiation is minimized while heat is applied to aspects of the tissue.

Yet another object of the invention is to provide a method for treating tumors. A feature of invention is that a medicament supporting substrate is reversibly received and reversibly immobilized within a housing, the latter of which may be stabilized within a patient's body via interactions of the surface of the housing with patient tissue. An advantage of the invention is that the minimization of displacement/rotation of either or both the substrate and housing allows irradiating only part of the lumen and avoiding other parts while simultaneously reducing the radiation to sites that may have a higher incidence of complications. Another advantage is that the radiation component could be after-loaded, thereby reducing medical personnel exposure. ("After-loading" is the placement of hollow structures (such as tubes, spheres, and other containment vehicles) into tumors, ducts, and cavities with the subsequent loading of these structures with radioactive material. This eliminates exposure of medical personnel to radiation during the surgical procedures of implantation of the tumor or intubation of a cavity.) The radioactive vehicle therefore defines a scaffold that is separate from the stent or housing and may be customized to the particular patient situation whereby the vehicle is fitted or attached to an appropriately sized stent or housing.

Briefly, the invention provides a system for the in vivo treatment of diseased tissue, the system comprising a first longitudinally extending surface and a second longitudinally extending surface coaxial to the first longitudinally extending surface to form a medicament carrying vehicle, wherein the vehicle defines a tunnel adapted to allow physiological fluid to pass through the vehicle.

An embodiment of the invention comprises a housing (or a plurality of housings and a medicament vehicle removably received by the housing. Generally, one vehicle is received by one housing, such that if more than one housing comprises a treatment system, then more than one vehicle is also utilized. However, a housing may be adapted to simultaneously receive and encapsulate more than one vehicle, for example two vehicles coaxially positioned relative to each other in a sleeve construed as the housing. Components of the system may be totally or partially removed, as clinically indicated.

The vehicle supports or otherwise contains radioactive isotope, for example cesium 131. The isotope is covered by a sealant, such that the sealant overlays the vehicle in an adherent film in regions where the isotope is found. As such, the sealant substantially completely encapsulates the isotope so as to prevent contact between the isotope and polar and nonpolar materials such as blood, saliva, water, urine, bile, and lipid. (The sealant is provided to prevent isotope leakage from the vehicle to the patient.) This radioisotope-sealant complex may further comprise a high z material such as bismuth. Alternatively, the high z material may be applied to proximal surfaces of the housing. The purpose of the high z material is to attenuate radiation emanating from the radioisotope. While the accompanying drawings depict tubes and generally cylindrical vehicles and housings, other shaped voids are also suitable housing shapes, so as to define spherical-, cuboidal- (including rectangular), ovoidal-, and pyramidal-, or slab-like voids. As such, the vehicles and their encapsulating housings may be spheres, cubes, ovals, pyramids, prisms, slabs, etc. The spheroidal or cuboidal or irregular shaped voids could be covered and sealed by silicone or similar sealant containing high z material exterior to a radio isotope in one or a plurality of layers.

For example, one such housing iteration is configured as a sleeve or hollow cylinder. A vehicle is slidably received by the sleeve, the vehicle also in the shape of a sleeve or hollow cylinder, but with a cross section diameter less than the housing. With the vehicle and sleeve coaxially arranged along their longitudinal axes, the resulting configuration defines an open channel which can accommodate fluid such as blood, food (in instances where the system is placed in the esophagus), feces, urine, inhaled and exhaled air, bile, and other physiological fluids.

Also provided is a method for treating, in vivo, diseased tissue, the method comprising inserting a housing into a tumor excision site and removably sliding a medicament vehicle within the housing so as to be encapsulated by the housing.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1A:
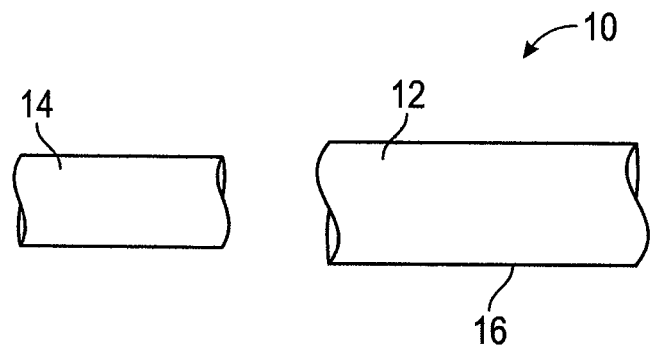
FIG. 1A is an exploded view of the system, in accordance with features of the present invention.

An in situ system and method for treating diseased tissue is provided. FIG. 1A is an exploded view of the invention, generally designated as numeral 10. A housing 12 defining a first cross section is in axial registration with a medicament support vehicle 14 defining a second cross section. Like the housing, 12, the medicament support vehicle 14 is hollow. The second cross section is less than the first cross section so that the vehicle is slidably received by the housing 12. In this configuration, the cylindrical void defined by the vehicle is concentrically and coaxially aligned with the cylindrical void defined by the housing 12. This will allow for a guide wire, extending through the hollow vehicle to effect movement of both the housing and vehicle simultaneously or sequentially.

Figure 3A:
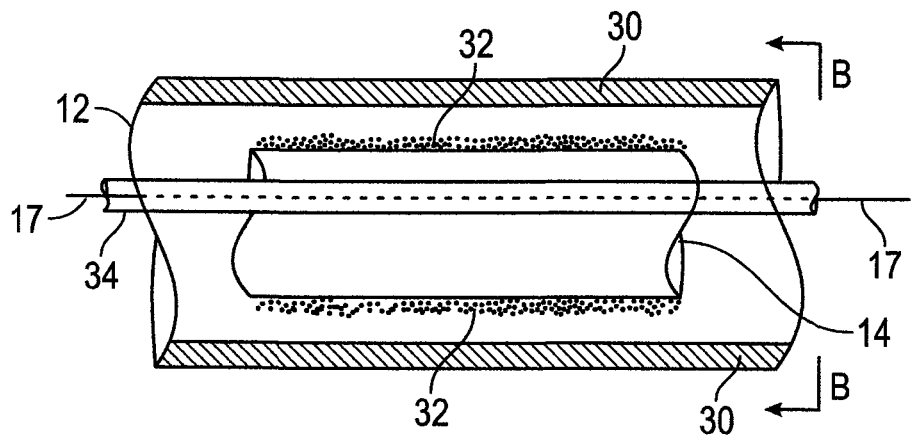
FIG. 3A is an elevational view of one embodiment of the system.
Figure 3B:
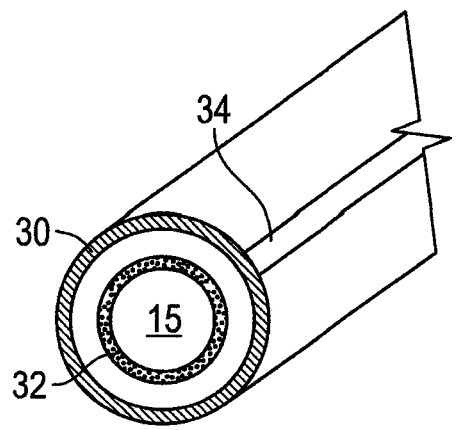
FIG. 3B is a view of FIG. 3A taken along line B-B.

Alternatively, and as depicted in FIGS. 3A and 3B, the guidewire may be adapted to be received by longitudinally extending exterior surfaces of the housing forming a tunnel 34. As such, the tunnel 34 rests upon and is supported by the exterior surfaces of the housing and may be integrally molded with the exterior surface of the housing. Alternatively, the tunnel may be a tubing adhered to, or reversibly fastened to, the exterior surface.

The housing 12 is depicted with a first and second end, both ends open. This to accommodate both physiological fluid passage and the system's transom along a guide wire (17 in FIG. 1B) in instances where the wire is used to slide the system into hard to reach physiological structures.

The exterior surface 16 of the housing 12 may be smooth, or roughened. A smooth surface may be utilized to facilitate removable insertion into narrow ducts and other physiological lumens. For example, a bifurcating housing 12 with a cross section of about 0.5 cm may be utilized to treat Klatskin tumors, which are carcinomas of the hepatic biliary tree.

Figure 2A:
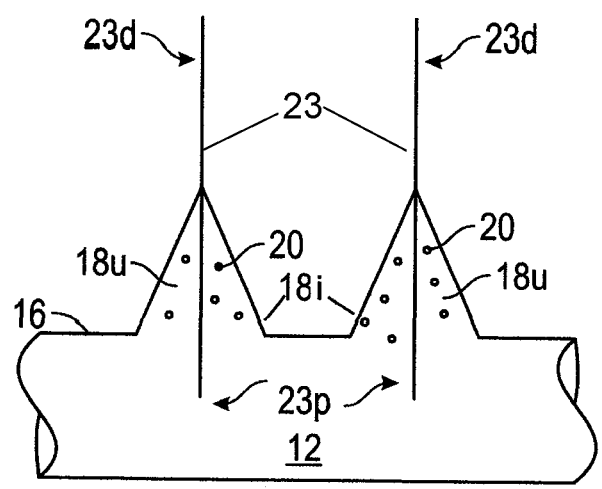
FIG. 2A is a detailed view of exterior surfaces of the housing of the system, in accordance with features of the present invention.
Figures 7A, 7B:
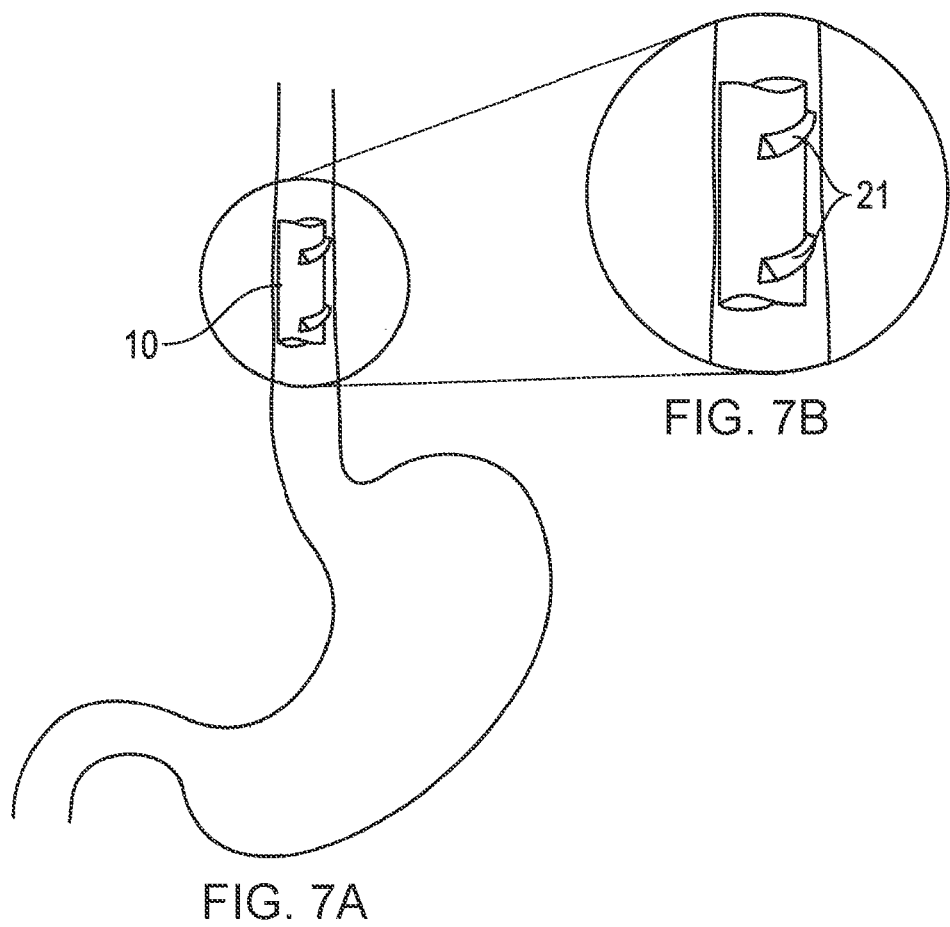
FIG. 7A is a schematic view of the invented system implanted in a human esophagus, in accordance with features of the present invention.
FIG. 7B is a close up of FIG. 7A, detailing the implanted system, in accordance with features of the present invention.

A roughed surface may be utilized to enhance anchoring of the system 10 to the tissue requiring treatment, such tissue including the esophagus (see FIG. 7A), the lower GI tract, the bronchus of the lungs, and the bladder. In esophageal treatments, a mid-point region of the housing 12 which directly overlays a vehicle housed within it may be positioned to oppose cancerous tissues and not normal esophageal mucosa. This will result in the cancerous tissues being in close spatial relationship, and even contacting corresponding exterior surfaces 16 of the housing As depicted in FIG. 2A, this mid-point region may support upright 18$u$ and inverted 18$i$ cones having arbitrary dimensions and angles relative to the longitudinally extending surface defining the exterior surface 16 of the housing.

Generally, the utilization of cones and other shapes results in an increase in total surface area of the exterior surface of the housing 12. If the area A of cone is equal to $(\pi\ r) \times (r\ l) + \pi\ r^2$ (wherein r=radius, and l=length) then a 1 mm diameter cone base and 1 mm height (length) will provide 1.75 mm$^2$ surface area. When 0.215 mm$^2$ is added for the regions where the base of the cone contacts the base of another cone at the exterior surface 16 of the housing 12 (thus forming a corner), a surface area of approximately 2 mm$^2$ per exterior surface of the cone is realized. So, for a 50 mm long housing 12 having a 10 mm radius, total surface area would equal 2 $\pi$ r×50 mm=314 sq. mm (mm$^2$) i.e. 2×10×3.14×50 mm=3140 sq. mm. In conclusion of this point, the simple addition of cones with above dimensions increases total surface area in this example from 3140 sq. mm to approximately 6000 sq. mm.

In another example, if a stent is 20 mm in diameter, then it has a surface area=pi radius square times length such that a 5 cm long interface has surface interface of 50×20 mm×pi or approximately 3000 cones, each cone providing approximately 3 interfacing sq. mm per cone plus adjacent edges. This results in approximately 6000 mm$^2$ of interfacing surface.

For example, given a cone with a base radius of ½ millimeter (mm) (i.e., diameter of 1 mm) and a height of 1 mm, therefore representing a cone angle of about 127 degrees. In this specification, the "cone angle" is twice its opening angle, the latter of which is typically considered the angle between the cone axis and its surface. As such, each opening angle defines a right angle triangle of approximately 60 degrees. Given these illustrative parameters, the original surface area defining the housing increases from 1 square mm underneath the cone to 2.54 square mm plus the flat surfaces between the cones. (Approximately 0.214 square mm increases the small square surface area from 1 square mm to closer to 2 square mm.) If the cone angle increases to 180 degrees but maintains its original radius so to approximate a cylinder, the relative surface area decreases but more relatively thinner (i.e., smaller angle) cones could be placed on the surface of the stent. Manufacturing and other practical issues may determine the ultimate density of the cones and inverted cones including the feasibility of an inherent drainage system which may ultimately clot, further increasing the resistance to slippage.

Cone sizes and/or diameters may need to be increased or decreased or otherwise modified when dealing with the small segmented pouches of bowel separated by haustral folds, those pouches referred to as haustra. The cones, and their associated ridges 21 may define different shaped triangles in cross section, including but not limited to equilateral triangles, isosceles triangles, right angle triangles (i.e., one angle 90 degrees), acute triangles (i.e., all angles less than 90 degrees), obtuse triangles (one angle more than 90 degrees), scalene triangles (no equal sides) and combinations thereof.

Figure 2B:
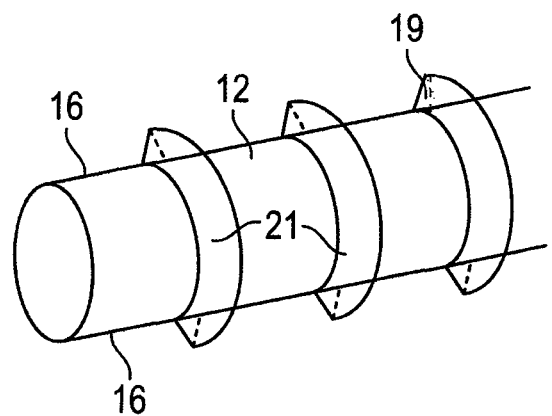
FIG. 2B is a perspective view of exterior surfaces of the housing, in accordance with features of the present invention.

Peristalsis in the esophagus and other parts of the digestive tract is a factor in stent slippage although it is often interrupted in areas of the esophagus cancer. About 50 percent of peristalsis are attenuated in the cancer. As such, shaping the cones (for example employing half-cone configurations (19 as shown in FIG. 2B) instead of full cone structures will leverage the circular muscle contractions embodied by the peristalsis so as to counter other forces such as bolus propulsion so as to keep the stent in place.

Alternatively, ridges 21 or radially directed fins or other shaped structures extending from exterior surfaces 16 of the housing may be used in anticipation of the return of peristaltic function after treatment. Similar peristaltic issues occur in the colon. The ridges may be straight so as to be parallel with the longitudinal axis of the housing 12, or they may be curved. The distal edge of the ridge may be straight, curved, or serrated or crenulated. The distal edges may be further treated with medicament, such as coagulant, antiseptic material, or material (such as bio-adhesive) to enhance frictional engagement with tissue.

In those situations in which there is peristalsis present which may be interrupted in areas of cancer, the cones could be shaped such that peristalsis would actually force the stent craniad. In one configuration, cones are shaped as half cones (such that their cross section defines right angle triangles) 19 so as to define right angles (as depicted in perspective view FIG. 2B) such that peristalsis pushes them cephalad. These half cones 19 may extend perpendicular to the longitudinal axis of the device 10 with a plurality of cones arranged over latitudinally extending exterior surfaces of the housing 16 to form the aforementioned ridges, 21. Or, these half cones may be discrete from each other, so as to form individual silos (depicted in FIG. 2A), with their longitudinal axes perpendicular to the longitudinal axis of the entire structure 10. The final number of ridges and cones, and or half cones etc., becomes a practical issue in part experimentally determined. These accessories may also act to prevent stent rotation and/or migration near areas in which radiation may cause fistulas. For example, one such problem area is where the left main bronchus crosses in front of the esophagus. Over-radiation or other type of over treatment of that area can lead to tracheo-esophageal (TE) fistulas. Pneumonia often results.

The cones may have apertures 20 formed in their sides. The insides (i.e., the interiors) of the cones are hollow so as to direct physiological fluids (which are initially contacting the exterior surfaces of the cones) to the inside of the housing, which is coaxial to the esophageal lumen. Ultimately, over time, the holes may be filled by in-grown tumor and serosanguinous fluids which may clot, further limiting the potential for slippage. Efforts to remove the stent so defining this surface structure may require the application of anti-coagulants or other means to reverse the pressure gradients. Also, if a separate radio-isotopic incorporating layer is present (for example, if the radioisotope exists solely within the vehicle housed by the housing acting as the stent, it may be removed separately, leaving the stent in place.

The aforementioned cones or half cones may be comprised of sealant material (e.g., silicone) which is molded to the exterior surface 16 of the stent, the silicone also used to encapsulate the high Z material located on the same surface 12 as discussed herein. In areas where the cones directly oppose cancerous tissue, the apex or tips of the cones may be sharp (i.e., define a tiny radius) or otherwise configured to actually impale proximal tumor tissue, causing bleeding, which in turn coagulates and helps stabilize the stent even more. Conversely, in areas where the cones directly oppose healthy parenchyma, the apices or tips of the cones may be blunted (e.g., define a relatively larger radius) so as not to puncture or otherwise harm that healthy tissue. The sharp apex or peak of the cone may become dull (i.e., blunt) over time (by either repeated use of the sleeve 12 or by being subjected to physiologic mechanisms such as peristalsis, friction engagement with tissue, fluid flow, etc. Alternatively, the apices may be dulled via chemical or mechanical treatment prior to insertion in a patient.

As in the Gecko reptile, instead of supporting cones, the surface of the housing 12 may support a plurality of cylinders, thus mimicking the hair-like structures (i.e. setae) of those creatures; so as to increase the surface area for enhanced engagement with the patient. This creates frictional interaction with proximal tissue surfaces (and potentially Van der Waals forces which are very weak polar forces). An advantage of this embodiment is its complete biocompatibility.

Alternatively, the system may include wicks 23 to facilitate clearance of physiological fluids which otherwise accumulate around the system 10. Generally, the wicks 23 extend away from tissue surfaces which emanate fluid and extend toward a drainage channel. One such channel may be the interior void defined by the cones. The wicks may extend in a direction orthogonal to the length of the guidewire. In an embodiment of this wicking feature, a distal end 23d of the wick (FIG. 2A, 2B) may contact or be in a close spatial relationship to the tissue being treated while an anchored proximal end 23p of the wick is where gathered fluid accumulates and sloughs off to be expedited through interior, longitudinally extending void defined by the housing 12 (as depicted in FIG. 2A) or along longitudinally extending exterior surfaces 16 of the housing (as depicted in FIG. 2B). FIG. 2B also shows the center channel 15 to accommodate the passage of physiological fluids, as discussed supra.

The cones may make it possible for the exterior surface 16 of the housing 12 to actually dig into the fleshy tumor. This would provide a means for preventing the housing from rotating such that increased thickness near the left main bronchus could produce a relative cold spot to minimize the fistulization risk.

Figure 2C:
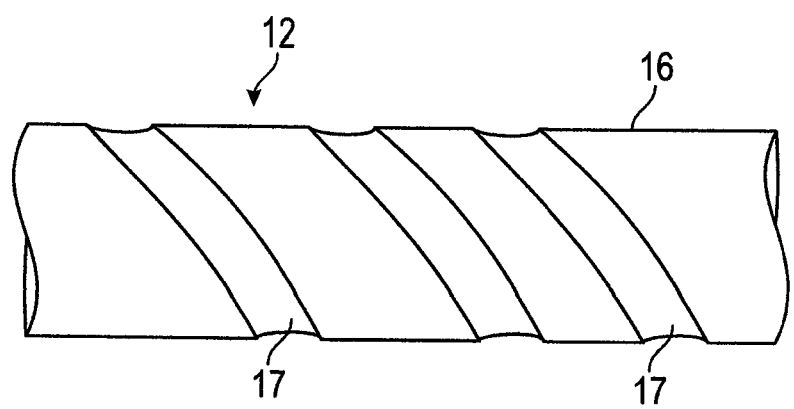
FIG. 2C is an isometric view of countersunk surfaces of the housing, in accordance with features of the present invention.

There may be instances where housings with decreased frictional engagement are desired. For example, the insertion of the system 10 in bone may require medicament containing 17 (FIG. 2C) of surfaces of the housing or sleeve to forming countersunk refions 17 relative to the remainder of the exterior surfaces of the sleeve. Such countersunk positioning would prevent the bone from scraping the medicament and sealant from the surfaces of the housing during installation and positioning of the system within a bone shaft (e.g., femur).

Despite this countersunk embodiment a salient object of invention remains, which is to say the provision of a multi-surface platform for the in vivo delivery of medicaments. The "sleeve" 12 of this embodiment overlays, protects or otherwise shields the medicament vehicle, which in this instance is the plurality of countersunk regions 17, seen in FIG. 2C as helical grooves. The grooves are shown as being helically shaped so as to facilitate rotation into and out of bone shafts. But the countersunk regions 17 may also be discrete chemically remote depressions in the surface 16 of the sleeve. These remote depressions may allow for the loading of different medicaments onto the same sleeve so that the medicaments do not physically contact each other.

The grooves may be filled with radioactive isotope and high z-materials (e.g., bismuth), then finally overlaid with sealant. As discussed above, the isotope and high z material may be mixed together, or applied separately to the countersunk regions 17.

Furthermore, the sleeve 12 may be hollow as described above, or it may be a solid substrate such as a bar, slab, rod, sphere, cube, or rectangle.

Figure 1B:
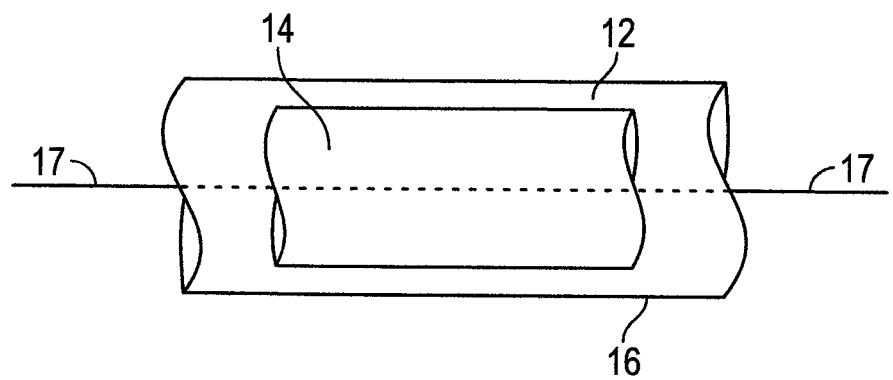
FIG. 1B is an elevational view of the system, in accordance with features of the present invention.

FIG. 1B shows the medicament support vehicle 14 contained within the housing 12. The vehicle is designed to be slidably and removably received by the housing. Depending on the cross section diameters of each of the housing 12 and the vehicle 14, the vehicle may be selected to impose friction fit between the vehicle and housing; in this instance, the outer diameter of the vehicle is only slightly less than the inner diameter of the sleeve so as to impart contact between the vehicle and the sleeve. This will provide a means to prevent rotation of the vehicle within the housing once positioned therein. However, there may be instances where the vehicle rotates within the housing, for example with the imposition of an AC current, to assure homogenization of dose application to all aspects of the housing. One method to impart rotation is akin to that of a rotor spinning within a stator, wherein the vehicle is the rotor and the housing is the stator. This method balances any irregularity in dose that may otherwise occur due to uneven distribution of radioisotope along the vehicle.

Medicament, Sealant, and Attenuation Substrate Detail

A salient feature of the invention is that liquid or powderized forms of medicament (e.g., isotopes) are utilized. For purposes of this specification, any discrete particles whose sizes are less than 1000 microns are considered powders, so less than No. 18 mesh. (Typically-sized radioactive seeds, with dimensions of about 1 mm×5 mm, are not preferred for use in this invention.) This allows flexibility in device design and dosage applications. For example, the invention provides flexibility of size and shape of the stents. Such uniquely shaped and miniaturized stents will accommodate the distal esophagus and gastric cardia, gastric pyloric area, bi- and tri-furcations as in the bronchial tree or bifurcation of hepatic ducts, (e.g., in the instance of Klatskin tumors).

Either the vehicle or the housing may support/deliver medicaments, nano-particles, such medications either integrally molded with aspects of the housing or substrate, or else adsorbed so as to be released in physiological conditions (such as body temperature, pH, osmotic gradient oxygen concentration, carbon dioxide concentration, glucose concentration, and the like).

For example, the chemical composition of the housing 12 may comprise semi rigid webbing such as nitinol, silicone, or other biocompatible material. Also the housing 12 may further comprise high z material (i.e., radiation attenuation material) selected from the group consisting of bismuth, titanium, chromium, vanadium, iron, aluminum, copper, salts of the above, alloys of the above, such as steel, other metal alloys, and combinations thereof. In this embodiment, the semi-rigid webbing material is homogeneously combined with the high Z material. Exemplary high Z material in this instance may be powderized bismuth chloride. This iteration allows for heating of the housing, either via electrical resistance or more remotely via EMF applications. For example, a means for inducing hyperthermia at the treatment site may including applying a voltage across the nitinol housing 12, or externally supplied by ultrasound RF.

Separate layer configurations may also be employed, wherein the outer layer of the housing 12 or sleeve would have high z material such as bismuth, such that the outer layer would overlay an inner layer comprising both silicone and radio-isotopes. The radio-isotopes may be integrally molded with the housing to allow for after-loading.

In an alternative embodiment, the exterior surface 16 of the housing 12 is covered with high Z material (e.g., bismuth), while interior surfaces of the housing are covered with radioisotope.

The vehicle 14 comprises radioisotope and high Z material (such as bismuth) to partially attenuate the undesirable radiations emanating from the isotope. As such, the radio-isotope and high Z material may be homogeneously mixed prior to coating same onto the surface of the vehicle 14. The entire surface of the vehicle may be so overlaid with the homogenous mixture, or just one side of the vehicle may be overlaid such that a second side of the vehicle facing in an opposite direction of the first overlaid side is not covered with the mixture.

Radioisotopes utilized in the mixture may include, but are not limited to, Cesium 131, Iodine 125, Palladium 103, Ytterbium 169, Samarium 153, and combinations thereof. It should be appreciated that entirely new isotopes as currently be developed or as clinical experience justifies, may be suitable radiation-emanating sources.

High Z material utilized in the mixture may include, but are not limited to bismuth, titanium, chromium, vanadium, iron, aluminum, copper and alloys such as steel, other alloys, and combinations thereof.

The materials comprising the medicament vehicle 14 may further be overlaid with a sealant. The sealant provides a means for preventing cloning off or leakage of the isotope from the vehicle. Generally, the sealant is a biocompatible material that is also waterproof and selected from the group consisting of silicone, bioglass, polyvinylchloride, polyethylene, polypropylene, ceramic (such as alumina, zirconia, and hydroxyapatite), polymethylmethacrylate, polytetrafluoroethylene, and combinations thereof.

It is noteworthy that a plurality of sealant layers, of the same type of sealant, or different sealants overlaying each other, can be utilized.

Example 1

The embodiment in this example, depicted in FIGS. 3A-B, comprises a housing and vehicle, wherein solely the vehicle supports radio-isotope. The housing 12 supports a layer 30 comprised of silicone and high z material such as bismuth. This embodiment allows after loading.

The radio-isotope may be supported on the exterior surfaces of the vehicle 14, either alone or mixed to form a film 32 overlaying the exterior surfaces of the vehicle. Optionally, the film may overlay all surfaces of the vehicle 14 including the interior surface of the vehicle (in instances where the vehicle defines a hollow cylinder), or homogeneously mixed with the material forming the vehicle. Advantages of this embodiment include the establishment of a buffer zone between exterior surfaces of the vehicle and inwardly facing surfaces of the encapsulation housing.

This arrangement further allows the vehicle to be placed within the housing at specific radial arc positions within the housing so that dosages may be directed toward one longitudinally extending surface of the housing and away from a second longitudinally extending surface of the housing. As such, the vehicle may be loaded with radio-isotope along one surface of the vehicle and not along a second surface of the vehicle. Accuracy of placement of the vehicle within the housing and of the entire system may be confirmed via dosimetry.

This embodiment may further comprise a housing supporting radioactive attenuation material, either coating the outside of the housing, the inside of the housing, or homogeneously dispersed as one of the constituent materials forming the housing.

The outer wall of the device which may be coated in silicone or a silicone-bismuth homogenized mixture may have geometrical shapes in order to increase the opposing surface areas. For example, if each square mm of the opposing surface had a cone of 1 mm diameter and height, the interfacing surface area increases from 1 mm square to approximately 2 square mm. This configuration results in the device impaling (at least temporarily, or reversibly) the tumor such that any serosanguinous material may pass into a central lumen of the cones and even clot, further keeping the device in place.

The cones could function to prevent rotational- as well as longitudinal-displacement.

Various strategies including wedges would prevent longitudinal slippage but be less effective to prevent rotations. More complex shapes could be accommodated by the outer layer with a silicone or similar materials.

Example 2

The embodiment in this example comprises a housing and vehicle, wherein both the housing and vehicle support radio-isotopes.

The radio-isotope supported by the housing may be different than the radio-isotope supported by the vehicle. For example, the radio-isotope supported by the housing may have a shorter half-life than the radio-isotope supported by the vehicle encapsulated by the housing. In this instance, the housing may further comprise radiation attenuation material.

Figure 4:
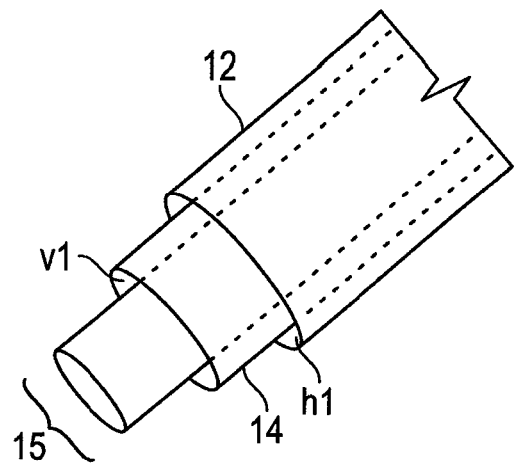
FIG. 4 is a perspective view of the system showing wall thicknesses of medicament vehicles and housings, in accordance with features of the present invention.

FIG. 4 shows this embodiment, wherein the housing 12 and vehicle 14 define walls having thicknesses, h1 and v1 respectively. Both of the thicknesses h1 and v1 are defined by layers of high z material and radio-isotope. The layers may be separate from each other so as to be discrete, such that the high z layer overlays the radio-isotope layer. Alternatively, the high z material may be mixed with the radio-isotope to form a homogeneous film which overlays both the housing 12 and the vehicle 14. (As in previous examples, the entire configuration forms a center passageway or channel 15 to accommodate physiological fluid flow.)

Optionally, the housing 12 is finally overlaid with a sealant such as silicone.

In an alternative embodiment of the rigid materials model, three layers are utilized: a middle layer is comprised of nitinol or other metallic substrate; an innermost layer (e.g., the vehicle 14) supports the medicament such as radio-isotope, and an outer layer would support high z material. The outer layer may be integrally molded with exterior surfaces of the middle layer such that the outer layer is a film overlaying the middle layer. The outer layer may comprise cones or other friction inducing surfaces made of high z material.

Figure 5:
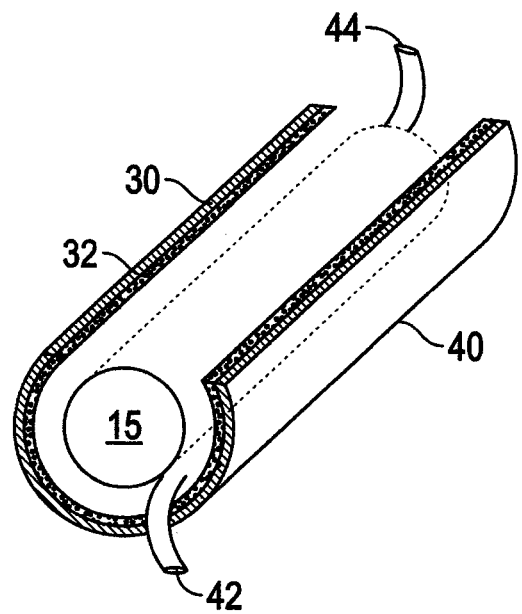
FIG. 5 is perspective view of a non-rigid medicament carrier, in accordance with features of the present invention.

Instead of the housing 12 comprising a rigid material (such as nitinol), it may be constructed of a flexible material, such as a leak proof webbing, such as polymer membrane. For example, as depicted in FIG. 5, the housing may comprise a cylinder shaped balloon 40 defining an axially extending tunnel adapted to allow physiological fluid to flow through its center 15. The balloon may be coated or otherwise overlaid with an isotope and high z material mixture comprising the film 32, as initially discussed supra and depicted in FIG. 3A-3B. This first overlayment may further overlaid with a sealant such as silicone 30.

The void defined by the balloon may be adapted to receive warm fluid such as saline as a means to produce hyperthermic conditions at the site of radiation treatment. As such, the balloon may have a fluid means of ingress 42 and a fluid means of egress 44. These ingress and egress means allow for fluid to be inserted into the balloon, both for thermal treatment, and also to expand the balloon to fill the site of tumor excision, thereby ensuring a snug fit against the patient.

Medially facing surfaces of the balloon 40 define the fluid passageway 15. Those surfaces may or may not be similarly overlaid with a radio-isotope/high z mixture comprising the film 32 and therefore a sealant material 30.

In summary, the balloon 40 defines a first longitudinally extending surface that faces outwardly and therefore toward tissues defining tumor excise sites. Being shaped as a tunnel, the balloon further defines a second longitudinally extending surface that faces medially and therefore towards the center of any physiological lumen the balloon is encapsulating.

While the balloon is depicted as a hollow cylinder or tunnel, other shaped balloons are also suitable, including cuboidal, spheroidal, rectangular or prismatic. These balloons may, like the tunnel shaped balloon discussed supra, have passageways in fluid communication with its surroundings, this to channel physiological fluids along whatever lumen, duct, organ or other structure in which the balloon is positioned. Alternatively, the balloons may define a single internally remote void only. However, exterior regions of the balloon may be invaginated or otherwise form channels to facilitate fluid traversal and routing along those exterior regions.

Figure 6:
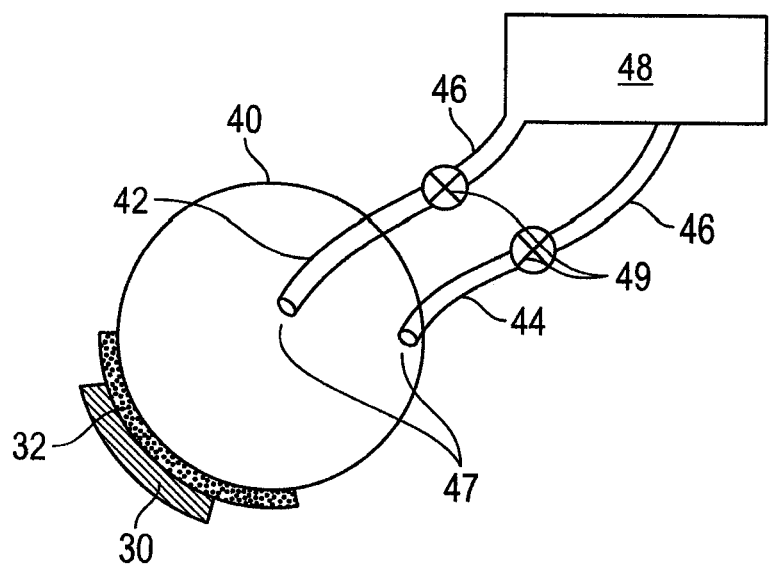
FIG. 6 is a cross section view of a non-rigid medicament carrier.

FIG. 6 depicts a balloon 40 shaped as a sphere. The balloon is solid in that it does not define transverse fluid passageways such as that passageway 15 depicted in the afore-described tunnel-shaped balloon, FIG. 5. However, its surface 19 may be overlaid with high-z material and isotope layer comprising the aforementioned film 32 and then sealant 30, as is the case with the balloon configuration depicted in FIG. 5. This leaves the interior void of the balloon open for hyperthermic applications. The anti-neoplastic effects of hyperthermia are DNA repair inhibition, changes in the micro-environment, and stimulation of immunity. Vascular thermos-tolerance suggests that fractionation will be beneficial. Increased blood flow may also result. Any tumor thermo-tolerance is thought to decay back to baseline after a few days. Generally, local hyperthermia treatment for deep seated tumors include circulating heated fluids, local heat source for intra-cavity applications, radiant heat (IR and visible), capacitive/inductive RF, micro waves, and magnetic heating of nano particles. For example, the practical electromagnetic range (wave length of 4 to 200 cm) has a potential penetration of 1-15 cm.

As with the configuration depicted in FIG. 5, the solid balloon embodiment depicted in FIG. 6 may have a fluid means of ingress 42 and/or egress 44, such means defining a conduit 46 or conduits. Proximal ends of these conduits may be in fluid communication with a warm or cool fluid reservoir 48. Distal ends 47 of the conduits may be inserted within the void defined by the balloon so as to allow the distal ends to be directed to various portions of the void to homogenize fluid temperatures within the void and prevent relatively cool or hot spots from developing.

In operation, the system may be loaded on to a guidewire endoscopically, radiographically, or into a trocar for placement inside of a patient's body. In one loading procedure, the housing 12 is first loaded onto the guidewire for eventual placement at the treatment venue. Once the housing placement is confirmed, the same guidewire may be used to position the vehicle 14 within the housing 12. This is often referred to as after-loading.

In another loading procedure, assembly is made remotely from the treatment site. For example, the vehicle 14 first may be placed within the housing 12 and then the entire assembly is loaded onto a guidewire for eventual placement at the treatment site. Or, like beads on a string, the housing 12 may first be loaded onto a guidewire, then the vehicle 14 loaded on the string.

Endoscopic visualization, ultrasound, or x-rays may be utilized to confirm ideal placement of the system proximal to diseased tissue identified in need of treatment.

Following endoscopic confirmation of carcinoma placement of the system may commence, either embodying a smooth conformal surface or a friction enhanced one, for example a surface supporting cone like projections to prevent slippage.

In instances where the device is too difficult to pass through the endoscope a guide wire may be needed. These instances may include the following:
  Bifurcating device: two or more guidewires are placed one in each intended lumens and the device is placed over it.
  Adjacent to areas at high risk for fistula production, e.g., left main bronchus or if the tumor is eccentric. Given the anti-rotation tendency of the cones, one could decrease the radiation as clinically appropriate.
  Areas near where there is differing luminal diameters such as GE junction (where most esophageal cancers occur) this could be accommodated.
  Optionally, and depending on the housing structure utilized, the system is reversibly anchored into the diseased tissue it is intended to treat.

Upon final placement, the system delivers a homogeneous, yet attenuated dose of radiation to the diseased tissue. Inasmuch as physical structures of the system are integrally molded with high z material, the exposure of adjacent healthy tissue to hot spots caused by radiation over exposure is eliminated. Simultaneously, exterior surfaces of the surface may impart heat to the diseased tissue at temperatures several degrees (e.g., approximately 3-4 degrees) above body temperature.

Once treatment is complete (which may be less than 1 to 7-26 weeks depending on the radio-isotope used or the progress of treatment and if low dose rate radiation is the modality), the system is removed from the original treatment venue and either discarded in accordance with environmental regulations, or repositioned in the patient or in another patient for further treatment. Alternatively, the system may remain in place permanently, if its position within the body is secured, as discussed above and radiation emanates from a single source of high activity, e.g., high dose radiation (HDR).

It is to be understood that the above description is intended to be illustrative, and not restrictive. For example, the above-described embodiments (and/or aspects thereof) may be used in combination with each other.

In addition, many modifications may be made to adapt a particular situation or material to the teachings of the invention without departing from its scope. For example, while radio-isotopes are described as the medicament in this specification, the invented vehicle may also be used to deliver non-radioactive benefits, such as in hormonal treatment, glucose regulation, and arrhythmia medications. Nanoparticles, including alpha particles, are also candidates.

While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A system for the in vivo treatment of diseased tissue, the system comprising a housing having a first longitudinally extending surface and a medicament support vehicle slidably received by the housing and defining a second longitudinally extending surface coaxial to the first longitudinally extending surface, wherein the vehicle defines a tunnel adapted to allow physiological fluid to pass through the vehicle and wherein the first longitudinally extending surface is-non-rigid and supports radially directed structures integrally molded thereto-wherein the radially directed structures have regions forming apertures to direct physiological fluids, which are initially contacting the radially directed structures, to the inside of the housing.

2. The system as recited in claim 1 wherein the first longitudinally extending surface support radiation attenuation material.

3. The system as recited in claim 1 wherein the medicament carrying vehicle carrier supports bismuth and radioactive isotope, wherein the bismuth and the radioactive isotope are encapsulated by a sealant.

4. The system as recited in claim 1 wherein the first longitudinally extending surface expands and contracts in a radial direction.

5. The system as recited in claim 1 wherein the tunnel may have a cross section shape selected from the group consisting of circular, rectangular, triangular, polygonal, and combinations thereof.

6. The system as recited in claim 1 wherein the first longitudinally extending surface defines an exterior surface adapted to frictionally interact with patient tissue to cause the tissue to excrete the physiological fluids.

7. The device as recited in claim 1 wherein the radially directed structures define shapes selected from the group consisting of upright cones, inverted cones, cylinders, and combinations thereof.

8. The device as recited in claim 1 wherein the radially directed structures are upright cones and the upright cones have a cross section that define shapes selected from the group consisting of equilateral triangles, isosceles triangles, right triangles, acute triangles, obtuse triangles, scalene triangles, and combinations thereof.

9. A device for the in situ treatment of cancerous tissue, the device comprising a sleeve and a medicament supporting vehicle adapted to be removably received by the sleeve while also allowing physiologic fluid to flow through it, wherein the sleeve supports high z material on an exterior surface wherein the exterior surface is defined by integrally molded and radially directed structures having apertures adapted to remove physiologic fluids emanating from the cancerous tissue.

10. The device as recited in claim 9 wherein the-radially directed structures reversibly attach the exterior surface to a patient's tissue so as to prevent slippage or rotation of the sleeve in situ.

11. The device as recited in claim 9 wherein a sealant overlays the high z material.

12. The device as recited in claim 9 wherein the vehicle is coaxial to the sleeve and the vehicle is adapted to slidably receive a guidewire.

* * * * *